United States Patent
Yu et al.

(10) Patent No.: US 11,084,799 B2
(45) Date of Patent: Aug. 10, 2021

(54) POLYMORPH OF BENZAMIDE COMPOUND AND PREPARATION METHOD AND APPLICATIONS THEREOF

(71) Applicant: SHENYANG SINOCHEM AGROCHEMICALS R&D CO., LTD., Liaoning (CN)

(72) Inventors: Haibo Yu, Liaoning (CN); Guimin Zhao, Liaoning (CN); Guosheng Zhang, Liaoning (CN); Junwu Ying, Liaoning (CN); Huibin Yang, Liaoning (CN); Bin Li, Liaoning (CN)

(73) Assignee: SHENYANG SINOCHEM AGROCHEMICALS R&D CO., LTD., Liaoning (CN)

(*) Notice: Subject to any disclaimer, the term of this patent is extended or adjusted under 35 U.S.C. 154(b) by 0 days.

(21) Appl. No.: 16/306,970

(22) PCT Filed: Jul. 27, 2017

(86) PCT No.: PCT/CN2017/094655
§ 371 (c)(1),
(2) Date: Dec. 4, 2018

(87) PCT Pub. No.: WO2018/019268
PCT Pub. Date: Feb. 1, 2018

(65) Prior Publication Data
US 2019/0144418 A1    May 16, 2019

(30) Foreign Application Priority Data
Jul. 27, 2016   (CN) .......................... 201610599227.1

(51) Int. Cl.
*A01N 43/40*   (2006.01)
*A01N 43/56*   (2006.01)
*C07D 401/04*   (2006.01)

(52) U.S. Cl.
CPC ........... *C07D 401/04* (2013.01); *A01N 43/40* (2013.01); *A01N 43/56* (2013.01); *C07B 2200/13* (2013.01)

(58) Field of Classification Search
CPC ..... A01N 43/40; A01N 43/56; C07B 2200/13
See application file for complete search history.

(56) References Cited

U.S. PATENT DOCUMENTS 8,492,409 B2    7/2013 Li et al.

FOREIGN PATENT DOCUMENTS

| CN | 101333213 A | 12/2008 |
| CN | 101747318 A | 6/2010 |
| CN | 102020633 A | 4/2011 |
| CN | 105801558 A | 7/2016 |
| WO | 2010/003350 A1 | 1/2010 |

OTHER PUBLICATIONS

Stieger et al. ("Recrystallization of Active Pharmaceutical Ingredients." North-West University, Unit for Drug Research & Development. South Africa. 2012) (Year: 2012).*
Yang et al. CN10202633 B2, IDS Dec. 4, 2018. Translation. (Year: 2011).*
International Search Report for PCT/CN2017/094655, dated Nov. 2, 2017 in English and Chineses Language.
Office Action for Chinese Patent Application No. 2016-10599227.1 dated Jan. 2, 2020 (with SIPO Search Report No. 2016105992271 dated Jul. 27, 2016.
Office Action for India Patent Application No. 2018-27045119 dated Sep. 30, 2019.
Office Action for Indonesia Patent Application No. P00201810432 dated Jan. 16, 2020 (3 pages with translation).
Supplementary European Search Report Application No. 17833571.7 dated Nov. 7, 2019.

* cited by examiner

*Primary Examiner* — Jeffrey S Lundgren
*Assistant Examiner* — Chris E Simmons
(74) *Attorney, Agent, or Firm* — Smith, Gambrell & Russell, LLP

(57) ABSTRACT

The present invention provides a polymorph of a benzamide compound and a preparation method and applications thereof. The shown benzamide compound is 3-Bromo-N-[2,4-dichloro-6-[(methylamino)carbonyl]phenyl]-1-(3,5-dichloro-2-pyridinyl)-1H-pyrazole-5-carboxamide. The application of the polymorph of the compound in the preparation of the formulation exhibits excellent effect. The advantages of the polymorph A in aspects such as chemical stability, filterability, solubility, hygroscopicity, melting point, solid density and flowability can have a significant impact on the developments of the production method and a formulation and on the quality and efficacy of a plant treating agent.

10 Claims, 1 Drawing Sheet

POLYMORPH OF BENZAMIDE COMPOUND AND PREPARATION METHOD AND APPLICATIONS THEREOF

FIELD OF THE INVENTION

The present invention belongs to the fields of insecticides and fungicides, and particularly relates to a polymorph of a benzamide compound and a preparation method and applications thereof.

BACKGROUND OF THE INVENTION

3-Bromo-N-[2,4-dichloro-6-[(methylamino)carbonyl]phenyl]-1-(3,5-dichloro-2-pyridinyl)-1H-pyrazole-5-carboxamide (Compound 1) has high insecticidal activity, and has been developed as an insecticide by Shenyang Sinochem Agrochemical R & D Co., Ltd. Tetrachlorantraniliprole is the common name of Compound 1. The specific chemical structure of the Compound 1 is as follows:

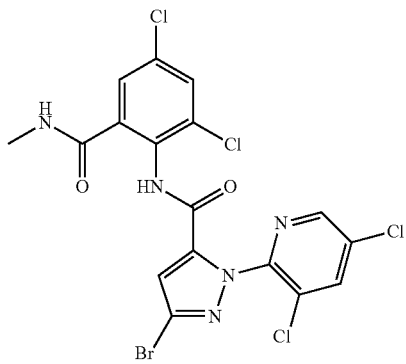

(Compound 1)

Tetrachlorantraniliprole

WO2010003350A1 and CN102020633A disclose methods for the preparation of 3-bromo-N-[2,4-dichloro-6-[(methylamino)carbonyl]phenyl]-1-(3,5-dichloro-2-pyridinyl)-1H-pyrazole-5-carboxamide (Compound 1), as well as the application of the compound as an insecticide.

Tetrachlorantraniliprole has excellent insecticidal effect, and is widely used and favored by farmers. However, with the development of science and technology, higher requirements are put forward for pesticide formulations. How to improve the performance of the formulation of Tetrachlorantraniliprole is an urgent work for the skilled artisan.

SUMMARY

The present invention aims to provide a new polymorph of 3-bromo-N-[2,4-dichloro-6-[(methylamino)carbonyl]phenyl]-1-(3,5-dichloro-2-pyridinyl)-1H-pyrazole-5-carboxamide (Compound 1), a preparation method thereof, and the applications of the new polymorph in controlling insect and plant disease.

To achieve the above purpose, the technical solution of the present invention is as follows:

A polymorph of a benzamide compound is provided, wherein the polymorph of the benzamide compound is a polymorph A of 3-bromo-N-[2,4-dichloro-6-[(methylamino)carbonyl]phenyl]-1-(3,5-dichloro-2-pyridinyl)-1H-pyrazole-5-carboxamide. By using Cu-Kα radiation, the polymorph A is characterized by x-ray powder diffraction pattern having the 2θ reflection positions: 10.24, 12.40, 17.84, 18.96, 19.12, 22.76, 23.92, 24.72, 25.92, 26.12, 28.64, 31.96, 34.00, 38.92, 42.20 and 46.24.

Optionally, by using Cu-Kα radiation, the polymorph A is characterized by x-ray powder diffraction pattern having at least 20 reflection positions:

| 2θ | 2θ | 2θ | 2θ |
| --- | --- | --- | --- |
| 10.6 | 18.48 | 23.76 | 31.56 |
| 11.28 | 18.52 | 25.24 | 32.48 |
| 12.88 | 19.28 | 25.36 | 32.52 |
| 12.92 | 19.36 | 25.44 | 32.56 |
| 12.96 | 19.4 | 27.76 | 33.68 |
| 13.56 | 19.44 | 28.08 | 36.84 |
| 13.6 | 19.48 | 28.12 | 36.88 |
| 15.64 | 19.52 | 28.88 | 36.92 |
| 15.96 | 19.64 | 28.92 | 39.76 |
| 16 | 20.68 | 29.92 | 39.8 |
| 16.04 | 21.24 | 30.12 | 39.88 |
| 16.48 | 23.48 | 30.2 | 44.72 |
| 17.16 | 23.56 | 30.24 | 44.8 |
| 17.36 | 23.6 | 30.28 | 49.36 |
| 18.36 | 23.68 | 31.52 | 54.4 |

Further optionally, the polymorph A has x-ray powder diffraction spectrum shown in FIG. 1.

A polymorph mixture of the benzamide compound is provided. The mixture consists of several polymorphs of 3-bromo-N-[2,4-dichloro-6-[(methylamino)carbonyl]phenyl]-1-(3,5-dichloro-2-pyridinyl)-1H-pyrazole-5-carboxamide.

The specific mixture includes the polymorph A of 3-bromo-N-[2,4-dichloro-6-[(methylamino)carbonyl]phenyl]-1-(3,5-dichloro-2-pyridinyl)-1H-pyrazole-5-carboxamide and the polymorph B of 3-bromo-N-[2,4-dichloro-6-[(methylamino)carbonyl]phenyl]-1-(3,5-dichloro-2-pyridinyl)-1H-pyrazole-5-carboxamide.

Optionally, by using Cu-Kα radiation, the polymorph B is characterized by x-ray powder diffraction pattern having the at least 20 reflection positions: 10.60, 11.28, 12.92, 13.56, 15.64, 16.48, 17.36, 18.48, 19.40, 20.68, 21.24, 23.68, 25.24, 27.76, 28.88 and 29.92.

Further optionally, the polymorph B has x-ray powder diffraction spectrum shown in FIG. 2.

The present invention also provides a preparation method for the polymorph of the benzamide compound, comprising: mixing the solid form of 3-bromo-N-[2,4-dichloro-6-[(methylamino)carbonyl]phenyl]-1-(3,5-dichloro-2-pyridinyl)-1H-pyrazole-5-carboxamide with solvent to form slurry to prepare the polymorph A after heating.

The solid form of 3-bromo-N-[2,4-dichloro-6-[(methylamino)carbonyl]phenyl]-1-(3,5-dichloro-2-pyridinyl)-1H-pyrazole-5-carboxamide comprises polymorph B of 3-bromo-N-[2,4-dichloro-6-[(methylamino)carbonyl]phenyl]-1-(3,5-dichloro-2-pyridinyl)-1H-pyrazole-5-carboxamide.

The above recorded polymorph B can be prepared in accordance with the method disclosed in CN102020633A. When acyl chloride is condensed with the aniline, the reaction solvent is selected from toluene. After the reaction is completed, the temperature is directly decreased to obtain the polymorph B.

Further optionally, in the preparation method, the step of mixing the solid form of 3-bromo-N-[2,4-dichloro-6-[(methylamino)carbonyl]phenyl]-1-(3,5-dichloro-2-pyridinyl)-1H-pyrazole-5-carboxamide with the solvent to form slurry also comprises adding the polymorph A to the slurry, in order to increase the rate of conversion from the solid form to the polymorph A in the reaction process.

Further optionally, the mass ratio of the solid form of 3-bromo-N-[2,4-dichloro-6-[(methylamino)carbonyl]phenyl]-1-(3,5-dichloro-2-pyridinyl)-1H-pyrazole-5-carboxamide to the solvent is 1:1-15.

Further optionally, the solid form of 3-bromo-N-[2,4-dichloro-6-[(methylamino)carbonyl]phenyl]-1-(3,5-dichloro-2-pyridinyl)-1H-pyrazole-5-carboxamide is mixed with the solvent to form the slurry, and the slurry is heated under stirring to a temperature between 30° C. and the boiling point of the solvent; the mixture is heated to reflux for 1-10 h; and then the slurry is cooled to 0-35° C. to obtain the polymorph A.

The mass ratio of the solid form of 3-bromo-N-[2,4-dichloro-6-[(methylamino)carbonyl]phenyl]-1-(3,5-dichloro-2-pyridinyl)-1H-pyrazole-5-carboxamide to the solvent is 1:3-12.

Further optionally, the solid form of 3-bromine-1-(3,5-dichlor-2-pyridyl)-N-[2,4-dichlor-6-[(methyl amino) carbonyl]phenyl]-1H-pyrazole-5-formylamine is mixed with the solvent to form the slurry, and the slurry is heated under stirring to 50° C.-110° C.; the mixture is heated to reflux for 2-6 h; and then the slurry is cooled to 0-30° C. to obtain the polymorph A.

The mass ratio of the solid form of 3-bromo-N-[2,4-dichloro-6-[(methylamino)carbonyl]phenyl]-1-(3,5-dichloro-2-pyridinyl)-1H-pyrazole-5-carboxamide to the solvent is 1:4-10.

Further optionally, the solid form of 3-bromo-N-[2,4-dichloro-6-[(methylamino)carbonyl]phenyl]-1-(3,5-dichloro-2-pyridinyl)-1H-pyrazole-5-carboxamide is mixed with the solvent to form the slurry, and the slurry is heated under stirring to 70° C.-90° C.; the mixture is heated to reflux for 4-10 h; and then the slurry is cooled to 20-25° C. to obtain the polymorph A.

The mass ratio of the solid form of 3-bromo-N-[2,4-dichloro-6-[(methylamino)carbonyl]phenyl]-1-(3,5-dichloro-2-pyridinyl)-1H-pyrazole-5-carboxamide to the solvent is 1:5-8.

The solvent is selected from an alcohol solvent and/or water.

The alcohol solvent can be selected from one or more of C1-C20 alcohols, and preferably one or more of methanol, ethanol, n-propanol, isopropanol, n-butanol and n-pentanol.

Preferably, the solvent is water and/or ethanol. When the water and the ethanol are mixed, the ratio by weight percentage is 4-1:1.

In the present invention, the slurry of the polymorph B of Compound 1 is heated in the presence of the solvent to convert into the polymorph A of Compound 1. The solvent is selected from the alcohol solvent and/or water. The alcohol solvent is selected from methanol, ethanol, n-propanol, isopropanol, n-butanol and n-pentanol. The adopted solvent can well convert the polymorph B into the polymorph A. In addition, the water as the solvent is well used to convert the polymorph B into the polymorph A. Furthermore, in the conversion process, at a temperature not more than 100° C., almost 100% conversion is completed at high yield within proper time. In the selection of the solvent, the water is selected to effectively reduce cost compared with the organic solvent. Moreover, the polymorph A has very low solubility in the water and can be easily separated through filtration. As an alternative, if the polymorph A with high concentration is in the water, then the polymorph A can be separated through evaporation of the water.

Further optionally, the above records that the mixture of the solid polymorph B of Compound 1 and water, in the form of a suspension or slurry, is placed inside a suitably sized vessel equipped with means of mixing and heating the mixture. Then, the mixture is heated with mixing to complete the conversion of the polymorph B to the polymorph A. Moreover, in the reaction system, before heating, seed crystals of the polymorph A are added to the mixture containing the polymorph B, which is more favorable for conversion from the polymorph B to the polymorph A, i.e., the conversion rate of the polymorph B is increased. The addition of seed crystals reduces the total conversion time and reduces the temperature required in the conversion process. After conversion of the polymorph B to the polymorph A is completely, the suspension is filtered to separate the solid compound. The solid product or wet pressed powder is further dried to obtain a crystal product which is suitable for preparing formulation compositions not containing water or directly used for preparing formulation compositions containing water (e.g., aqueous suspension).

The polymorph of a formylamine compound can be prepared through various forms and has the characteristics of raw material of the polymorph. The solid forms include crystal forms, wherein component molecules are arranged in ordered and repeated patterns in all of three spatial dimensions. It can be seen that the polymorph A of Compound 1 can exhibit excellent effects at the aspects of the preparation of the formulation and improvement of biological performance relative to another polymorph of the compound 1 or mixture of polymorphs.

The advantages of the polymorph A in aspects such as chemical stability, filterability, solubility, hygroscopicity, melting point, solid density and flowability can have a significant impact on the developments of the production method and a formulation and on the quality and efficacy of a plant treating agent. Specifically, researchers find that the polymorph B, when exposed to changing air humidity, has obvious hygroscopicity. Unlike the polymorph B, the polymorph A does not present obvious hygroscopicity characteristic when the air humidity changes. Furthermore, during long-term storage, the polymorph A has excellent stability and does not convert into other crystal forms. The stability is favorable for determination of consistency of Compound 1. These features enable the polymorph A of Compound 1 to be well suitable for preparing a long effective and stable solid formulation so that the polymorph A has stable content of active component.

X-ray powder diffraction is used to identify the crystallized phases of both polymorphs A and B of Compound 1, by using Philips X'PERT automatic powder diffractometer and Cu-Kα radiation (45 Kv, 40 mA). Samples were prepared as a dry smear on a low background glass specimen holder. Data were collected at 2θ angles from 10 to 90 degrees through continuous scanning with an equivalent step size of 0.03 degree and a count time of 2.0 seconds in per step.

2θ X-ray maxima values for polymorph A of Compound 1 are tabulated in Table 1.

TABLE 1

| 2θ | 2θ | 2θ | 2θ |
|---|---|---|---|
| 10.24 | 22.64 | 26.16 | 35.92 |
| 12.32 | 22.72 | 26.2 | 38.88 |
| 12.36 | 22.76 | 26.56 | 38.92 |
| 12.4 | 22.8 | 26.6 | 39.04 |

TABLE 1-continued

| 2θ | 2θ | 2θ | 2θ |
|---|---|---|---|
| 12.44 | 22.84 | 26.64 | 39.08 |
| 17.84 | 22.88 | 27.44 | 42.2 |
| 17.88 | 22.92 | 28.6 | 42.48 |
| 18.84 | 22.96 | 28.64 | 42.84 |
| 18.88 | 23.88 | 28.68 | 46.24 |
| 18.92 | 23.92 | 29.48 | 46.36 |
| 18.96 | 23.96 | 31.88 | 47.84 |
| 19 | 24.68 | 31.96 | 50.64 |
| 19.04 | 24.72 | 32 | 51.36 |
| 19.08 | 24.76 | 32.08 | 51.92 |
| 19.12 | 24.8 | 32.12 | 52.08 |
| 20.24 | 24.84 | 34 | 55.52 |
| 21.04 | 25.92 | 34.16 | |
| 21.76 | 26.12 | 35.92 | |

2θ X-ray maxima values for polymorph B of Compound 1 are tabulated in Table 2

TABLE 2

| 2θ | 2θ | 2θ | 2θ |
|---|---|---|---|
| 10.6 | 18.48 | 23.76 | 31.56 |
| 11.28 | 18.52 | 25.24 | 32.48 |
| 12.88 | 19.28 | 25.36 | 32.52 |
| 12.92 | 19.36 | 25.44 | 32.56 |
| 12.96 | 19.4 | 27.76 | 33.68 |
| 13.56 | 19.44 | 28.08 | 36.84 |
| 13.6 | 19.48 | 28.12 | 36.88 |
| 15.64 | 19.52 | 28.88 | 36.92 |
| 15.96 | 19.64 | 28.92 | 39.76 |
| 16 | 20.68 | 29.92 | 39.8 |
| 16.04 | 21.24 | 30.12 | 39.88 |
| 16.48 | 23.48 | 30.2 | 44.72 |
| 17.16 | 23.56 | 30.24 | 44.8 |
| 17.36 | 23.6 | 30.28 | 49.36 |
| 18.36 | 23.68 | 31.52 | 54.4 |

Meanwhile, the polymorphs A and B of Compound 1 are characterized by infrared spectroscopy. Specifically, the infrared spectroscopy is determined by using Impact400 type infrared spectrometer. Infrared spectroscopy data of the polymorph A of Compound 1 are listed in Table 3. Infrared spectroscopy data of the polymorph B of Compound 1 are listed in Table 4.

TABLE 3

Infrared Spectroscopy Data of Polymorph A:

| Wave Number (cm$^{-1}$) | Wave Number (cm$^{-1}$) | Wave Number (cm$^{-1}$) | Wave Number (cm$^{-1}$) |
|---|---|---|---|
| 3427 | 1684 | 1408 | 877 |
| 3193 | 1643 | 1357 | 838 |
| 3139 | 1567 | 1295 | 749 |
| 3057 | 1530 | 1119 | 609 |
| 2921 | 1500 | 1019 | 568 |
| 2851 | 1469 | 962 | 508 |

TABLE 4

Infrared Spectroscopy Data of Polymorph B:

| Wave Number (cm$^{-1}$) | Wave Number (cm$^{-1}$) | Wave Number (cm$^{-1}$) | Wave Number (cm$^{-1}$) |
|---|---|---|---|
| 3300 | 1667 | 1313 | 962 |
| 3143 | 1537 | 1272 | 889 |
| 3056 | 1463 | 1170 | 872 |
| 2975 | 1410 | 1131 | 852 |
| 2940 | 1380 | 1070 | 838 |
| 1682 | 1353 | 1022 | 741 |

The polymorph B of the compound is further characterized through X-ray single-crystal diffraction. The compound 1 (0.1 g) was added to toluene (5 ml), and the obtained clear solution slowly evaporates at room temperature to obtain massive colorless crystals of the polymorph B. Single crystals of about 0.28 mm×0.22 mm×0.20 mm are selected from the massive colorless crystals for use in a diffraction experiment. Cell parameters are set as: a=15.3311(16)Å, b=16.7319(16)Å and a=19.6687(19)Å, volume=4825.2(8) Å$^3$. The range of 2θ angle is equal to 1.50-26.00 by decreasing the date. The number of diffraction data amounts to 26933, wherein 9492 (R$_{int}$=0.037) are independent diffraction data. 9492 observable reflections (I>2σ(I)) are used for structure determination and correction. All calculation is implemented through the procedure of SHELXL-97 to obtain final deviation factors R=0.0468 and wR=0.1069. Atom fraction coordinates (×10$^4$) and equivalent isotropic displacement parameters are listed in Table 5 and Table 6, wherein U(eq) is defined as one third of orthogonal Uij trace of tensor, and the estimated standard deviation is in the bracket.

TABLE 5

Atom Coordinates (×10$^4$) and Equivalent Isotropic Displacement Parameters (Å$^2$ × 10$^3$) of Polymorph B of Compound 1

| Atom | X | Y | Z | U(eq) |
|---|---|---|---|---|
| Br(1) | 2542(1) | 4294(1) | 3872(1) | 109(1) |
| Br(1) | 293(1) | 1400(1) | 1667(1) | 88(1) |
| Cl(1) | −472(1) | 7181(1) | 6477(1) | 115(1) |
| Cl(2) | −1009(1) | 5758(1) | 3943(1) | 119(1) |
| Cl(3) | −1768(1) | 6759(1) | 1815(1) | 69(1) |
| Cl(4) | −1520(1) | 9650(1) | 737(1) | 107(1) |
| Cl(5) | 767(1) | −1084(1) | 5876(1) | 71(1) |
| Cl(6) | 2075(1) | 1574(1) | 4999(1) | 68(1) |
| Cl(7) | 4105(1) | 3120(1) | 4824(1) | 70(1) |
| Cl(8) | 7578(1) | 2236(1) | 5498(1) | 65(1) |
| O(1) | 332(2) | 7505(1) | 3599(1) | 54(1) |
| O(2) | 1789(2) | 7851(2) | 2086(1) | 59(1) |
| O(3) | 3430(2) | 472(1) | 4381(1) | 44(1) |
| O(4) | 4656(2) | 504(1) | 3267(1) | 53(1) |
| N(1) | 1163(2) | 6592(1) | 5338(2) | 56(1) |
| N(2) | 1008(2) | 5984(2) | 4252(1) | 45(1) |
| N(3) | 1534(2) | 5323(2) | 4436(2) | 59(1) |
| N(4) | 218(2) | 6938(2) | 2532(1) | 43(1) |
| N(5) | 1668(2) | 8818(2) | 2833(2) | 48(1) |
| N(6) | 1063(2) | −439(2) | 4032(2) | 43(1) |
| N(7) | 1557(2) | 686(2) | 3571(1) | 39(1) |
| N(8) | 809(2) | 741(2) | 3002(2) | 48(1) |
| N(9) | 3735(2) | 1661(2) | 3947(1) | 42(1) |
| N(10) | 5390(2) | −244(2) | 4203(1) | 42(1) |
| C(1) | 813(3) | 6843(3) | 5848(2) | 65(1) |
| C(2) | −82(3) | 6808(3) | 5798(2) | 68(1) |
| C(3) | −671(3) | 6486(3) | 5205(2) | 75(1) |
| C(4) | −316(3) | 6212(3) | 4678(2) | 61(1) |
| C(5) | 599(3) | 6290(2) | 4767(2) | 45(1) |
| C(6) | 1784(3) | 5159(3) | 3870(2) | 60(1) |
| C(7) | 1439(3) | 5684(2) | 3319(2) | 51(1) |
| C(8) | 932(2) | 6212(2) | 3573(1) | 40(1) |
| C(9) | 456(2) | 6942(2) | 3247(2) | 38(1) |
| C(10) | −201(2) | 7599(2) | 2111(2) | 38(1) |
| C(11) | −1119(2) | 7583(2) | 1749(2) | 44(1) |
| C(12) | −1522(3) | 8211(3) | 1321(2) | 55(1) |

TABLE 5-continued

Atom Coordinates (×10⁴) and Equivalent Isotropic Displacement Parameters ($A^2 \times 10^3$) of Polymorph B of Compound 1

| Atom | X | Y | Z | U(eq) |
|---|---|---|---|---|
| C(13) | −1018(3) | 8866(2) | 1279(2) | 56(1) |
| C(14) | −109(3) | 8912(2) | 1642(2) | 49(1) |
| C(15) | 300(2) | 8270(2) | 2052(2) | 38(1) |
| C(16) | 1311(2) | 8285(2) | 2342(2) | 39(1) |
| C(17) | 2641(3) | 8931(3) | 3106(2) | 61(1) |
| C(18) | 868(3) | −842(2) | 4555(2) | 48(1) |
| C(19) | 1060(3) | −543(2) | 5228(2) | 46(1) |
| C(20) | 1466(3) | 194(2) | 5381(2) | 49(1) |
| C(21) | 1646(2) | 621(2) | 4839(2) | 43(1) |
| C(22) | 1443(2) | 277(2) | 4173(2) | 38(1) |
| C(23) | 1099(2) | 1169(2) | 2551(2) | 48(1) |
| C(24) | 2004(2) | 1389(2) | 2794(2) | 45(1) |
| C(25) | 2287(2) | 1073(2) | 3459(2) | 37(1) |
| C(26) | 3203(2) | 1038(2) | 3977(2) | 38(1) |
| C(27) | 4651(2) | 1741(2) | 4352(2) | 36(1) |
| C(28) | 4913(2) | 2429(2) | 4754(2) | 42(1) |
| C(29) | 5806(2) | 7584(2) | 5109(2) | 46(1) |
| C(30) | 6451(2) | 2023(2) | 5089(2) | 43(1) |
| C(31) | 6211(2) | 1310(2) | 4733(2) | 40(1) |
| C(32) | 5315(2) | 1173(2) | 4357(2) | 36(1) |
| C(33) | 5089(2) | 445(2) | 3896(2) | 39(1) |
| C(34) | 5218(3) | −998(2) | 3828(2) | 60(1) |
| C(35) | 8294(6) | 8443(6) | 3111(3) | 117(3) |
| C(36) | 7407(7) | 8358(5) | 2980(3) | 111(2) |
| C(37) | 8649(7) | 9098(9) | 2956(5) | 155(5) |
| C(38) | 8087(15) | 9704(7) | 2663(5) | 210(9) |
| C(39) | 7195(14) | 9686(11) | 2520(7) | 257(14) |
| C(40) | 6868(6) | 8976(8) | 2685(5) | 159(4) |
| C(41) | 7061(9) | 7583(7) | 3146(5) | 246(6) |

TABLE 6

Hydrogen Coordinates (×10⁴) and Equivalent Isotropic Displacement Parameters ($A^2 \times 10^3$) of Polymorph B of Compound 1

| Atom | X | Y | Z | U(eq) |
|---|---|---|---|---|
| H(4) | 325 | 6514 | 2321 | 52 |
| H(5) | 1312 | 9110 | 2997 | 58 |
| H(6) | 3502 | 2042 | 3659 | 50 |
| H(10) | 5699 | −244 | 4642 | 50 |
| H(1) | 1205 | 7053 | 6259 | 78 |
| H(3) | −1291 | 6453 | 5160 | 90 |
| H(7) | 1532 | 5678 | 2872 | 62 |
| H(12) | −2133 | 8186 | 1065 | 66 |
| H(14) | 225 | 9368 | 1611 | 59 |
| H(17A) | 2939 | 8421 | 3160 | 91 |
| H(17B) | 2775 | 9194 | 3558 | 91 |
| H(17C) | 2853 | 9255 | 2782 | 91 |
| H(18) | 593 | −1341 | 4459 | 57 |
| H(20) | 1615 | 399 | 5839 | 59 |
| H(24) | 2341 | 1686 | 2558 | 54 |
| H(29) | 5969 | 3059 | 5358 | 55 |
| H(31) | 6650 | 922 | 4746 | 48 |
| H(34A) | 4719 | −1265 | 3936 | 90 |
| H(34B) | 5751 | −1328 | 3971 | 90 |
| H(34C) | 5070 | −902 | 3327 | 90 |
| H(35) | 8674 | 8024 | 3319 | 140 |
| H(37) | 9276 | 9149 | 3044 | 186 |
| H(38) | 8350 | 10170 | 2553 | 252 |
| H(39) | 6824 | 10116 | 2325 | 308 |
| H(40) | 6242 | 8915 | 2589 | 190 |
| H(41A) | 6677 | 7350 | 2720 | 369 |
| H(41B) | 6716 | 7662 | 3480 | 369 |
| H(41C) | 7562 | 7231 | 3348 | 369 |

The present invention provides a formulation. The formulation may include the polymorph A, a carrier and at least one adjuvant. Preferably, the formulation is a dispersoid. For example, these chemical formulations can be prepared into wettable powder or aqueous solution. In these compositions, at least one liquid or solid carrier is added, and appropriate surfactants may be added when required.

The present invention also provides an insecticidal composition, including the polymorph A as the active component. The weight percentage of the insecticidal composition in the active component is 1-99%. The insecticidal composition also comprises acceptable carriers in agriculture, forestry or public health.

The present invention also provides a fungicidal composition including polymorph A as the active component. The weight percentage of the fungicidal composition in the active component is 1-99%. The fungicidal composition also comprises acceptable carriers in agriculture, forestry or public health.

The insecticidal composition and the fungicidal composition according to the present invention can also further comprise other active components and/or auxiliary materials. For example, the insecticidal composition can include other insecticidal active components, and the fungicidal composition can include other fungicidal components.

The present invention also provides applications of the polymorph A for controlling insect pest and plant disease.

The technical solution of the present invention also comprises a method for controlling insect pest, which is to apply the polymorph A or its composition to the pest or growth medium of the pest. The more appropriate effective dose which is often selected is 10 to 1000 grams per hectare, and preferably, the effective dose is 20 to 500 grams per hectare.

The present invention also provides a method for controlling plant disease, comprising applying the polymorph A or its composition to the plant disease or growth medium of the plant disease. The more appropriate effective dose which is often selected is 100 to 2000 grams per hectare, and preferably, the effective dose is 200 to 1000 grams per hectare.

The technical solution of the present invention is suitable for controlling various important pests in agriculture and forest, stored grain insect and urban sanitary pests including holotrichia parallela, holotrichia diomphalia bates, anomala corpulenta, anomala exoleta, gryllotalpa orientalis burmeister, gryllotalpa unispina saussure, gryllotlp unispin sussure, agrotis ypsilon, agrotis segetum, agrotis tokionis, pleonomus canaliculatus, agriotes fuscicollis miwa, gryllusmitratus burmeister, teleogryllus emma, teleogryllus infernalis, sympiezomias velatus, stibaropus formosanus takado et yanagihara, opatrum subaratum faldermann, gonocephalum reticulatum motschulsky, bradysia odoriphaga yang et zhang, hylemyia platura meigen, chinese cabbage moth, onion fly, hyiemyia pilip ygavilleneuve, rice thrips, tobacco thrips, anaphothrips obscurus, Lissorhoptrus oryzophilus, Lissorhoptrus oryzophilus kuschel, tryporyza incertulas, sesamia inferens, sesamia inferens walker, taiwai muscosalis, oulema oryzae, rice root weevil, Lissorhoptrus oryzophilus, pachnephorus lewisii baly, beanblisterbeetle, psylliodes attenuata koch, rice leaf roller, parnara guttata, Nilaparvata lugens, sogatella furcifera, Laodelphax striatellus, rice leafhopper, oxya chinensis, orseoia oryzae, rice black bug, rice green caterpillar, nephotettix cinciceps, erythroneura subrufa, cicadella viridis, erythroneura sp., erythroneura sudra, nephotettix virescens, chlorita biguttula, recilia dorsalis, lycorma delicatula, cryptotympana atrata fabricius, rice midge, chlorops oryzae matsumura, hydrellia griseola, ephydramacellaria egg, sitobion avenae, schizaphis graminum, rhopalosiphum padi, Rhopalosiphum maidis, acarus hordei, mythimna separata, sitodiplosis mosellana gehin, homoeosoma electellum, mampava bipunctella ragonot, european wheat stem maggot, wheat sawfly, locusta migratoria manilensis, locusta migratoria migratoria, locusta migratoria tibetensis chen, oxya intricata, haplotropis brunneriana sauss, epacromius coerulipes, shirakiacris shirakii, calliptamus abbreviatus, pararcyptera micropatera merideonalis, oedaleus decorus asiaticus, oedaleus infernalis saussure, acrida cinerea, atractomorpha sinensis bolivar, aiolopus tamulus, myrmeleotettix palpalis, bryodema luctuosum luctuosum, Ostrinia nubilalis, valley flea beetle, proceras venosatus, Melanaphis sacchari, dryocosmus kuriphilus yasumatsu, herse convolvuli, brachmia macroscopa meyrick, loxostege sticticalis, chilotraea infuscatellus, sweetpotato weevil, phthorimaea operculella zell, soybean pod borer, maruca testulalis geyer, etiella zinckenella, melanagromyza sojae, clanis bilineata tsingtauica, melanagromyza dolichostigma de meijere, bradybaena ravida, bradybaena similaris, limax, Aphis gossypii glover, tetranychus cinnabarinus, green stink bug, adelphocoris suturalis, adelphocoris lineolatus, adelphocoris fasciaticollis reuter, dolycoris baccarum, halyomorpha halys, stephanitis nashi esaki et takeya, Pectinophora gossypiella, sylepta derogata fabricius, locastra muscosalis, *Helicoverpa armigera*, anomis flava, sylepta derogata fabricius, chlorita biguttula, Thrips tabaci, earias fabia stoll, earias cupreoviridis walker, earias insulana, Myzus persicae, lipaphis erysimi, brevicoryne brassicae, soybean aphid, peanut aphid, Acyrthosiphon pisum, uroleucon formosanum, Pieris rapae, colias erate, papilio xuthus, papilio polytes, Plutella xylostella, Spodoptera exigua, prodenia litura, mamestra brassicae, plusia agnata staudinger, ilattia cephusalis walker, hellula undalis fabricius, phyllotreta striolata fabricius, henosepilachna vigintioctomaculata, henosepilachna vigintioctopunctata, aulacophora indica, wheat sawfly, liriomyza sativae blanchard, liriomyza bryoniae kaltenbach, liriomyza huidobrensis, liriomyza trifolii, manduca sexta, leucoptera scitella, lithocolletis ringoniella, lyonetia clerkella, acrocercops astanrola, rhynchites foreipennis, aulacophora femoralis, Bemisia tabaci, trialeurodes vaporariorum westwood, polyphagotarsonemus latus banks, phaedon, thrips palmi kamy, diaphania indica saunders, saccharosydne procerus, cryptothelea variegata, cnidocampa flavescens walker, parasa consocia, porthesia similis, Hyphantria cunea drury, spilarctia subcarnea, phalera flavescens, ascotis selenaria, culcula panterinaria bremer et grey, sucra jujuba chu, percnia giraffata, cotton pearl scale, drosicha corpulenta, parthenolecanium corni bouche, eulecanium kuwanai, ceroplastes japonicus green, pseudococcus comstocki kuwana, cottoney apple scale, soybean root scale, eriococcus kaki kuwana, nipaecoccus vastator maskell, grape mealybug, lopholeucaspis japonica cokerell, pseudaulacaspis pentagona, lepidosaphes ulmi., unaspis yanonensis, Icerya purchasi maskell, didesmococcus koreanus borchs, anoplophora chinensis, marunba gaschkewitschii bremer et grey, apriona germari, anoplophora glabripennis, aromia bungii, batocera horsfieldi, bacchisa fortunei, grape tiger longicorn, thyestilla gebleri faldermann, oberea japonica thumb, phytoecia rufiventris, nola distributa walker, grape owlet moth, ampelophaga rubiginosa bremer et grey, paranthrene regale butler, phylloxera, aphis citricola van der goot, eriosoma lanigerum, macrosiphum rosirvorum zhang, schizaphis piricola, aphanostigma jakusuiense, lachnus tropicalis, tuberculatus margituberculatus, toxoptera citricidus, grapholitha molesta, carposina niponensis walsingham, janus piri okamoto et muramatsu, sinitinea pyrigalla yang, cossus cossus linnaeus, zeuzera coffeae niether, conopia hector butler, lampra limbata gebler, agrilus mali mats., grapholita funebrana, spilonota albicana matsumura, adoxophyes congruana walker, acleris fimbriana thunberg, adoxophyes cyrtosema meyrick, telphusa chloroderces meyrich, hyponomeuta malinellus, illiberis pruni, contarinia datifolia jiang, spilonota lechriaspis, carposina sasakii, dichocrocis punctiferalis, psylla chinese yang et li, aleurocanthus spiniferus quaintance, panonychus citri mcgregor, eotetranychus kankitus ehara, phyllocoptruta oleivora ashmead, aceria sheldoni, tetranychus viennesis zacher, tetrangchus urticae koch, Panonychus ulmi, tetranychus truncatus ehara, petrobia latens muller, oligonychus ununguis, brevipalpus obovatus donnadieu, epitrimerus zizyph-agus keifer, rhizoglyphus echinopus, penthaleus major, Phyllocnistis citrella stainton, to bactrocera dorsalis, diaphorina citri kuwayama, conopomorpha sinensis bradley, tessaratoma papillosa drury, aceria litchii keifer, aristobiafestudovoet, chlumetia transversa, banana root borer, persimm fruit worm, atrijuglans hetaohei yang, alcidodes juglans chao, curculio davidi fairmaire, chilo infuscatellus snellen, tetramoeraschistaceanasnellen, tryporyzanivellafabricius, alissonot μm impressicolle arrow, ceratovacuna lanigera zehntner, fulmekiola serrata, sugarcane mealybugs, sitophilus zeamais, rhizopertha dominica, trogoderma granarium everts, saw toothed grain beetle, rice weevil, araecerus fasciculatus, callosobruchus maculatus, ephestia elutella, ephestia kuehniella, aglossa dimidiata hswoth, aphomia gulariszeller, pyralis farinalis, cryptolestes pusillus, tribolium castaneum, cadelle, saw toothed grain beetle, rice flat grain, tribolium microhylidae, cryptolestes turcicus, cryptolestes ferrugineus, alphitobius diaperinus, tenebrio obscurus, Tenebrio molitor, callosobruchus chinensis, bruchus pisorum, bruchus rufimanus boheman, plodia interpunctella, sitotroga cerealella olivier, plodia interpunctella, almond moth, booklice, tyrophagus putrescentiae, carpophilus dim idiatus, pineapplebug, lasioderma serricorne, stegobium paniceum, trogoderma variabile, trogoderma glabrum, ptinus japonicus reitter, gibbium aequinoctiale boieldieu, housefly, greenbottle fly, lucilia, calliphoridae, flesh-fly, phormia regina, Blattella germanica, periplaneta americana, periplaneta japonica, periplaneta australasiae, periplaneta fuliginosa, periplaneta brunnea burmeister, pyenoscelus surinamensis, red ant, monomorium pharaonis, monomorium floricola, anopheles, culex and aedes.

The term "polymorph" refers to a specific crystal form of the compound (i.e., the structure of the lattice) that can exist in a solid state and in more than one crystal form.

The present invention has the following advantages:

The present invention provides a new solid polymorph A of 3-bromo-N-[2,4-dichloro-6-[(methylamino)carbonyl]phenyl]-1-(3,5-dichloro-2-pyridinyl)-1H-pyrazole-5-carboxamide (Compound 1). A polymorph of Compound 1 exhibits an excellent effect in aspects such as the use in preparing a preparation. The advantages of the polymorph A in aspects such as chemical stability, filterability, solubility, hygroscopicity, melting point, solid density and flowability can have a significant impact on the developments of the production method and a preparation and on the quality and efficacy of a plant treating agent. Unlike the polymorph B, the polymorph A does not present obvious hygroscopicity characteristic when the air humidity changes. Furthermore, during long-term storage, the polymorph A has excellent stability and may not be converted into other crystal forms. These features enable the polymorph A of Compound 1 to be well suitable for preparing a long effective and stable solid formulation so that the polymorph A has stable content of active component.

DETAILED DESCRIPTION OF THE INVENTION

As stated in the background, to enhance pesticide performance, the persons skilled in the art need to further develop the existing pesticide to enhance the pesticide performance.

It is well known in the art that some crystal compounds can exist as the polymorph. The term "polymorph" relates to specific crystalline forms of compounds crystallized in different crystalline forms. These crystalline forms have different molecular arrangements or conformations in lattices. Although the polymorphs have the same chemical composition, the polymorphs can also have different compositions due to existence of co-crystallized water or other molecules, which can be weakly or strongly bond in the lattice. The polymorphs can have different chemical, physical and biological characteristics, such as crystalline shape, density, hardness, chemical stability, melting point, hygroscopicity, suspendability, dissolution rate and bioavailability.

In the existing study on tetrachlorantraniliprole pesticide, although WO2010003350A1 and CN102020633A disclose that Compound 1 exists in the solid form, the emergence and number of the polymorphs of the tetrachloraniliprole pesticide have not been predicted so far and it is difficult to predict specific physicochemical characteristics of any polymorph. In the present invention, the inventors develop tetrachlorantraniliprole and provide a polymorph of tetrachlorantraniliprole. Compared with the existing known form of the tetrachlorantraniliprole, the polymorph has the more prominent advantages in aspects such as chemical stability, filterability, solubility, hygroscopicity, melting point, solid density and flowability can have a significant impact on the developments of the production method and a preparation and on the quality and efficacy of a plant treating agent. Thus, the polymorph is well suitable for preparing a long effective and stable solid formulation so as to increase the content of stable active components of the solid formulation of the pesticide.

Without further elaboration, it is believed one skilled in the art using the preceding description can utilize the present invention to its fullest extent. The following examples, therefore, to be construed as merely illustrative and not limiting of the disclosure in any way whatsoever. Specific examples of the polymorph A of Compound 1 are given below.

Example 1

Preparation of Polymorph A of Compound 1 (Using Water as the Solvent)

Figure 1:
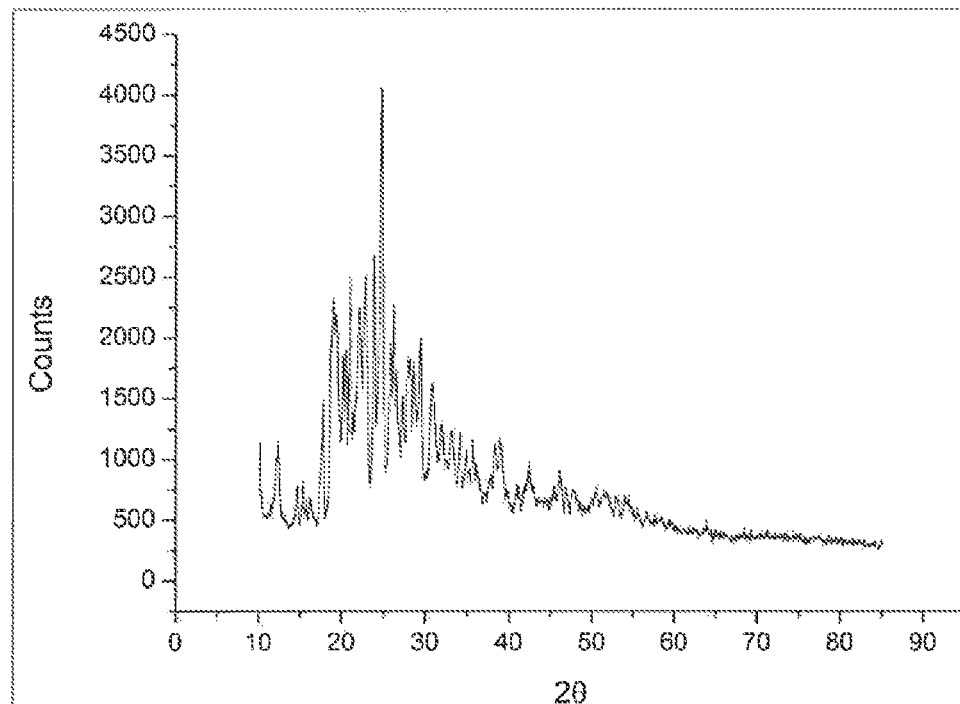
FIG. 1 is a X-ray powder diffraction pattern of polymorph A of Compound 1 provided in embodiments of the present invention, showing absolute intensity count garphed against 2θ reflection positions.
Figure 2:
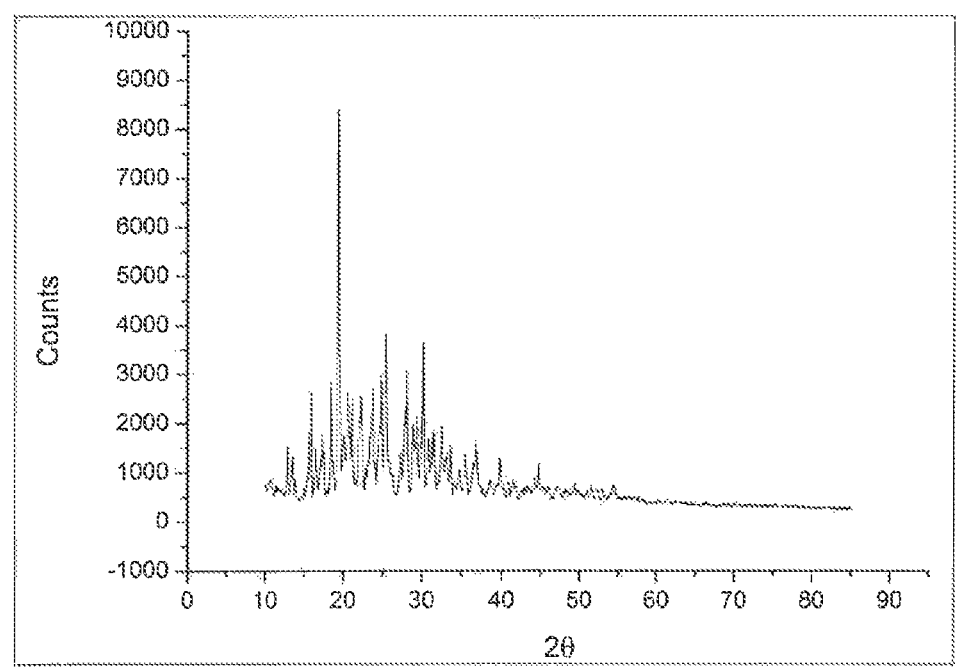
FIG. 2 is a X-ray powder diffraction pattern of polymorph B of Compound 1 provided in embodiments of the present invention, showing absolute intensity count garphed against 2θ reflection positions.

210 g of Water was added to the 500 mL of reaction bottle, then pressed powder of polymorph B of Compound 1 (70 g, in accordance with the method disclosed in CN102020633A, a reaction solvent was selected from toluene when acyl chloride was condensed with aniline, and after the reaction was completed, the temperature was directly reduced to 0° C., then filtered (see FIG. 2)) was added and the mixture was heated to reflux. After 5 hours the reactor was allowed to cool to 25° C., then the reaction mixture was filtered and dried to obtain the polymorph A (see FIG. 1) (64.0 g, the content of polymorph A is 98% by infrared analysis).

Example 2

Preparation of Polymorph A of Compound 1 (Using Water as the Solvent)

250 g of Water was added to 500 mL of reaction bottle, then pressed powder of polymorph B of Compound 1 (75 g, in accordance with the method disclosed in CN102020633A, a reaction solvent was selected from toluene when acyl chloride was condensed with aniline, and after the reaction was completed, the temperature was directly reduced to 0° C., then filtered) was added. The polymorph A (2 g) as seed crystal was added to the mixture. The mixture was heated to reflux. After 4 hours the reactor was allowed to cool to 25° C., then the reaction mixture was filtered and dried to obtain the polymorph A (68.3 g, the content of polymorph A is 98.2% by infrared analysis).

Example 3

Preparation of Polymorph A of Compound 1 (Using Ethanol as the Solvent)

200 g of ethanol was added to 500 mL of reaction bottle, then pressed powder of polymorph B of Compound 1 (35 g, in accordance with the method disclosed in CN102020633A, a reaction solvent was selected from toluene when acyl chloride was condensed with aniline, and after the reaction was completed, the temperature was directly reduced to ° C., then filtered, further post-treatment is not required) was added. The mixture was heated to reflux for 8 hours. The reactor was allowed to cool to 0° C.; then the reaction mixture was filtered and dried to obtain the polymorph A (25.8 g, the content of polymorph A is 96.8% by infrared analysis).

Example 4

Preparation of Polymorph A of Compound 1 (Using Ethanol as the Solvent)

200 g of Ethanol was added to the 500 mL of reaction bottle; then pressed powder of polymorph B of Compound 1 (35 g, in accordance with the method disclosed in CN102020633A, a reaction solvent was selected from toluene when acyl chloride was condensed with aniline, and after the reaction was completed, the temperature was directly reduced to 0° C., then filtered, further post-treatment was not required) was added. The polymorph A (2 g) as seed crystal was added to the mixture. The mixture was heated to reflux. After 4 hours the reactor was allowed to cool to 0° C., then the reaction mixture was filtered and dried to obtain the polymorph A (26.2 g, the content of polymorph A is 97.2% by infrared analysis).

Example 5

Preparation of Polymorph A of Compound 1 (Using Ethanol/Water as the solvent)

100 g of Ethanol and 100 g of water were added to the 500 mL of reaction bottle, then pressed powder of polymorph B of Compound 1 (72 g, in accordance with the method disclosed in CN102020633A, a reaction solvent was selected from toluene when acyl chloride was condensed with aniline, and after the reaction was completed, the temperature was directly reduced to 0° C., then filtered, further post-treatment was not required) was added. The polymorph A (2 g) as seed crystal was added to the mixture. The mixture was heated to reflux. After 4 hours the reactor was allowed to cool to 0° C., then the reaction mixture was filtered and dried to obtain the polymorph A (65.0 g, the content of polymorph A is 98.0% by infrared analysis).

Example 6

Preparation of Polymorph A of Compound 1 (Using n-Propanol as the Solvent)

200 g of n-Propanol was added to the 500 mL of reaction bottle, then pressed powder of polymorph B of Compound 1 (35 g, in accordance with the method disclosed in CN102020633A, a reaction solvent was selected from toluene when acyl chloride was condensed with aniline, and after the reaction was completed, the temperature was directly reduced to 0° C., then filtered, further post-treatment was not required) was added. The mixture was heated to reflux for 10 hours. The reactor was allowed to cool to 0° C.; then the reaction mixture was filtered and dried to obtain the polymorph A (24.2 g, the content of polymorph A is 96.4% by infrared analysis).

Example 7

In the processing of the formulation, the polymorph A has better physical properties than the polymorph B, such as better suspensibility and better pourability. In addition, the polymorph A also has better pharmacodynamic stability, such as better insecticidal activity. Comparison data of formulation performance of the polymorphs A and B are listed in Table 7. The polymorph A also presents better performance than the compound 1 prepared by the method (example 5) in the patent WO02010003350A1 in the aspect of the physical properties of the formulation. Comparison data are listed in Table 8.

The formulation includes the following composition: 10 parts of polymorph A of Compound 1 or polymorph B of Compound 1 obtained in above examples, 3 parts of sodium naphthalenesulfonate formaldehyde condensate, 3 parts of sodium salt of alkyl naphthalene sulfonic acid polycondensate, 0.1 part of white carbon black, 0.1 part of xanthan gum, 2 parts of pesticide emulsifier 0201B, 5 parts of glycol, 0.2 part of WJX-1 and water which is used to complement up to 100 parts by weight were successively added to a mixing tank for mixing. After conducting coarse grinding and homogenization through high shear, the mixture was grinded in a sand mill and detected the particle size of sanding materials through a sedimentograph. After the particle size meeting the standard requirements, the mixture was filtered to obtain 10% water suspending agent of polymorph A of Compound 1 or polymorph B of Compound 1.

TABLE 7

Comparison Data of Formulation Performance of Polymorphs A and B

| Comprehensive Physical Property | Polymorph B | Polymorph A |
| --- | --- | --- |
| Kept at normal temperatures | Observed after kept for 2 h, the formulation sample of the suspending agent is solidified and could not shake. | After kept for two years, the formulation sample of the suspending agent has good flowability and almost unchanged viscosity. |
| Heat storage (54 ± 2° C.) | Observed after heat storage for 1 h, the formulation sample of the suspending agent is solidified and could not shake. | After kept for 14 days (at 54 ± 2° C.), the formulation sample of the suspending agent has good flowability and almost unchanged viscosity. |
| Pourability | The formulation sample of the suspending agent does not flow; after poured, its residues are unqualified, and after washed, the residues are unqualified. | The formulation sample of the suspending agent has good flowability; after poured, the residues are less than or equal to 5%, and after washed, the residues are less than or equal to 0.5%; the pourability is qualified. |
| Particle size distribution | After kept at normal temperature for 1 week, big particles are increased and particle size distribution is wide. | After kept at normal temperature for 2 years and subjected to heat storage (54 ± 2° C./14 d), the particle size distribution is almost unchanged. |
| Dispersibility | After kept at normal temperature for 2 h, the formulation sample of the suspending agent is poor in dispersibility and difficult to shake. | After kept at normal temperature for 2 years and subjected to heat storage (54 ± 2° C./14 d), the formulation sample has good dispersibility and good flowability. |

TABLE 8

Comparison Data of Formulation Performance of Polymorph A and Compound 1 Prepared by the Method in WO2010003350A1

| Comprehensive Physical Property | Compound 1 Prepared by the Method in WO2010003350A1 | Polymorph A |
|---|---|---|
| Kept at normal temperatures | After kept for 1 week, the formulation sample of the suspending agent has poor flowability. | After kept for 2 years, the formulation sample of the suspending agent has good flowability and almost unchanged viscosity. |
| Heat storage (54 ± 2° C.) | Observed after heat storage for 3 days, the formulation sample of the suspending agent is solidified and could not shake. | After kept for 14 days (at 54 ± 2° C.), the formulation sample of the suspending agent has good flowability and almost unchanged viscosity. |
| Pourability | The formulation sample of the suspending agent has poor flowability; after poured, residues are unqualified, and after washed, the residues are unqualified. | The formulation sample of the suspending agent has good flowability; after poured, the residues are less than or equal to 5%, and after washed, the residues are less than or equal to 0.5%; the pourability is qualified. |
| Particle size distribution | Particle size distribution is wide. | After kept at normal temperature for 2 years and subjected to heat storage (54 ± 2° C./14 d), the particle size distribution is almost unchanged. |
| Dispersibility | After kept at normal temperature for 1 week, the formulation sample of the suspending, agent is poor in dispersibility and difficult to shake. | After kept at normal temperature for 2 years and subjected to heat storage (54 ± 2° C./14 d), the formulation sample has good dispersibility and good flowability. |

Moreover, the polymorphs are obtained through the above fabrication. The composition and the formulation by using the polymorph as the active component can control various important pests in agriculture and forest, stored grain insect and urban sanitary pests. The composition and the preparation are applied, in the existing manner, to lepidoptera pests, such as Ostrinia nubilalis, mythimna separata, Spodoptera exigua, agrotis ypsilon, mamestra brassicae, rice leaf roller, Chilo suppressalis, tryporyza incertulas, Cydia pomonella, carposina niponensis walsingham, grapholitha molesta, *Helicoverpa armigera*, anarsia lineatella and phthorimaea operculella zell; coleopteran pests, such as Lissorhoptrus oryzophilus kuschel, holotrichia parallela, holotrichia diomphalia bates, anomala corpulenta and anomala exoleta; homopteran pests, such as macrosiphum pisi, aphis craccivora, Aphis gossypii glover, aphis pomi, black bean aphid, wheat aphid, Nilaparvata lugens, sogatella furcifera, Laodelphax striatellus, rice leafhopper, nephotettix cincticeps, erythroneura subrufa, cicadella viridis, erythroneura sp., erythroneura sudra and nephotettix virescens; acarina pests, such as panonychus citri mcgregor, eotetranychus kankitus ehara, phyllocoptruta oleivora ashmead, aceria sheldoni, tetranychus viennesis zacher, tetrangchus urticae koch, Panonychus ulmi, tetranychus truncatus ehara, petrobia latens muller, oligonychus ununguis, brevipalpus obovatus donnadieu, epitrimerus zizyph-agus keifer, rhizoglyphus echinopus and penthaleus major; blattodea pests, such as Blattella germanica, periplaneta americana, periplaneta japonica, periplaneta australasiae, periplaneta fuliginosa, periplaneta brunnea burmeister and pyenoscelus surinamensis; thysanoptera pests, such as Thrips tabaci, rice thrips, tobacco thrips and anaphothrips obscurus; and hymenoptera pests, such as red ant, monomorium pharaonis and monomorium floricola. All of these plants have corresponding activities, under the dose of 30-60 grams per hectare, the above obtained substances have more than 80% of control effect on Plutella xylostella, beet armyworm, adoxophyes congruana walker, cabbage caterpillar, rice leaf roller, Chilo suppressalis, Ostrinia nubilalis, agrotis ypsilon, carposina niponensis walsingham and *Helicoverpa armigera*.

We claim:

1. A polymorph of a benzamide compound, wherein the polymorph of the benzamide compound is a polymorph A of benzamide compound of 3-bromo-N-[2,4-dichloro-6-[(methylamino)carbonyl]phenyl]-1-(3,5-dichloro-2-pyridinyl)-1H-pyrazole-5-carboxamide; by using Cu—Kα radiation, the polymorph A is characterized by x-ray powder diffraction pattern having the 2θ reflection positions: 10.24, 12.40, 17.84, 18.96, 19.12, 22.76, 23.92, 24.72, 25.92, 26.12, 28.64, 31.96, 34.00, 38.92, 42.20 and 46.24.

2. The polymorph of the benzamide compound according to claim 1, wherein the polymorph A has x-ray powder diffraction spectrum shown in FIG. 1.

3. A preparation method for a polymorph of 3-bromo-N-[2,4-dichloro-6-[(methylamino)carbonyl]phenyl]-1-(3, 5-dichloro-2-pyridinyl)-1H-pyrazole-5-carboxamide, comprising mixing a solid form of the benzamide with solvent to form a slurry containing recoverable amounts of polymorph A, a crystalline polymorph characterized by x-ray powder diffraction pattern having 2θ reflection positions: 10.24, 12.40, 17.84, 18.96, 19.12, 22.76, 23.92, 24.72, 25.92, 26,12, 28.64, 31,96, 34.00, 38.92, 42.20 and 46.24, using Cu—Kα radiation;

wherein the solid form of the benzamide includes polymorph B of 3-bromo-N42,4-dichloro-6-[(methylamino)carbonyl]phenyl]-1-(3,5-dichloro-2-pyridinyl)-1H-pyrazole-5-carboxamide;

where the polymorph B is characterized by x-ray powder diffraction pattern having the 2θ reflection positions: 10.60, 11.28, 12.92, 13.56, 15.64, 16.48, 17.36, 18.48, 19.40, 20.68, 21.24, 23.68, 25.24, 27.76, 28.88 and 29.92, using Cu—Kα radiation.

4. A preparation method for a polymorph of 3-bromo-N42,4-dichloro-6-[(methylamino)carbonyl]phenyl]-1-(3,5-dichloro-2-pyridinyl)-1H-pyrazole-5-carboxamide, comprising mixing a solid form of the benzamide with solvent under suitable conditions to form a slurry containing recoverable polymorph A, a crystalline polymorph characterized by x-ray powder diffraction pattern having 2θ reflection positions: 10.24, 12.40, 17.84, 18.96, 19.12, 22.76, 23.92, 24.72, 25.92, 26,12, 28.64, 31,96, 34.00, 38.92, 42.20 and 46.24, using Cu—Kα radiation;

wherein the solid form of 3-bromo-N42,4-dichloro-6-[(methylamino)carbonyl]phenyl]-1-(3,5-dichloro-2-pyridinyl)-1H-pyrazole-5-carboxamide includes polymorph B;

where the polymorph B is characterized by x-ray powder diffraction pattern having the 2θ reflection positions: 10.60, 11.28, 12.92, 13.56, 15.64, 16.48, 17.36, 18.48, 19.40, 20.68, 21.24, 23.68, 25.24, 27.76, 28.88 and 29.92, using Cu—Kα radiation and wherein the step of mixing the solid form of 3-bromo-N-[2,4-dichloro-6-[(methylamino)carbonyl]phenyl]-1-(3,5-dichloro-2-pyridinyl)-1H-pyrazole-5-carboxamide with the solvent to form slurry further comprises adding the polymorph A to the slurry.

5. The preparation method for the polymorph of the benzamide compound according to claim 3, wherein after the solid form of 3-bromo-N42,4-dichloro-6-[(methylamino)carbonyl]phenyl]-1-(3,5-dichloro-2-pyridinyl)-1H-pyrazole-5-carboxamide is mixed with the solvent to form the slurry, the slurry is heated under stirring to a temperature between 30° C. and the boiling point of the solvent; the mixture is heated to reflux for 1-10 h; and then the slurry is cooled to 0-35° C. to obtain the polymorph A.

6. The preparation method for the polymorph of the benzamide compound according to claim 5, wherein after the solid form of 3-bromo-N[2,4-dichloro-6-[(methylamino)carbonyl]phenyl]-1-(3,5-dichloro-2-pyridinyl)-1H-pyrazole-5-carboxamide is mixed with the solvent to form the slurry, and the slurry is heated under stirring to 50° C.–110° C.; the mixture is heated to reflux for 2-6h; and then the slurry is cooled to 0-30° C. to obtain the polymorph A.

7. The preparation method for the polymorph of the benzamide compound according to claim 3, wherein the solvent is selected from an alcohol solvent and/or water.

8. A formulation, wherein comprises the polymorph of the benzamide compound according to claim 1 as an active component.

9. An insecticidal and fungicidal composition, which comprises the polymorph of the benzamide compound according to claim 1 as an active component.

10. An application of the polymorph of the benzamide compound according to claim 1, which is the application of the polymorph A in controlling insect and plant disease.

\* \* \* \* \*